United States Patent [19]

Stupp et al.

[11] Patent Number: 5,412,144
[45] Date of Patent: May 2, 1995

[54] ORGANIC MATERIALS WITH NONLINEAR OPTICAL PROPERTIES

[75] Inventors: Samuel I. Stupp, Champaign; Sehwan Son, Savoy, both of Ill.; Hong-Cheu Lin, Taipei, Taiwan, Prov. of China

[73] Assignee: The Board of Trustees of the Univ. of Illinois, Urbana, Ill.

[21] Appl. No.: 180,405

[22] Filed: Jan. 12, 1994

[51] Int. Cl.$^6$ .................. C07C 255/33; C07C 69/767
[52] U.S. Cl. ..................... 558/406; 359/328; 359/329; 526/285; 560/59
[58] Field of Search ................. 558/406; 560/59

[56] References Cited

PUBLICATIONS

S. I. Stupp et al., *New Photonic Materials: Self Assembling Noncentrosymmetric Films and Two-Dimensional Polymers*, American Chemical Society Polymer Preprints, vol. 33, No. 2, p. 373 (1992).

J. S. Moore and S. I. Stupp, *Materials Chemistry of Chiral Macromolecules Synthesis and Phase Transitions*, Journal of the American Chemical Society, vol. 114, No. 9, pp. 3429-3441.

*Primary Examiner*—Joseph Paul Brust
*Attorney, Agent, or Firm*—Dressler, Goldsmith, Shore & Milnamow, Ltd.

[57] ABSTRACT

The present invention is directed to organic materials that have the ability to double or triple the frequency of light that is directed through the materials. Particularly, the present invention is directed to the compound 4-[4-(2R)-2-cyano-7-(4'-pentyloxy-4-biphenylcarbonyloxy)-phenylheptylidene)phenylcarbonyloxy]benzaldehyde, which can double the frequency of light that is directed through the compound. The invention is also directed to the compound (12-hydroxy-5,7-dodecadiynyl) 4'-[(4'-pentyloxy-4-biphenyl)carbonyloxy]-4-biphenylcarboxylate, and its polymeric form. The polymeric form can triple the frequency of light directed through it.

2 Claims, 5 Drawing Sheets

ORGANIC MATERIALS WITH NONLINEAR OPTICAL PROPERTIES

This invention was made with Government support under Contract No. DE-FG02-91ER45439 awarded by the Department of Energy. The Government has certain rights in this invention.

TECHNICAL FIELD

The present invention is directed to organic materials that form crystals or crystalline films having nonlinear optical properties, and the use of such materials to double or triple the frequency of light from a light source such as a laser.

BACKGROUND OF THE INVENTION

Materials that possess the ability to efficiently double or triple the frequency of light from a light source such as a laser are useful in the fabrication of electro-optical devices in which information storage or processing involves the modulation and switching of light beams.

Inorganic materials are known which double the frequency of laser beams, but these materials have a number of disadvantages, which include difficult or expensive processing, high dielectric constants, and electro-optic coefficients that are not high enough for some applications.

In view of the significant disadvantages of these inorganic materials, it would be useful to develop new materials to overcome those limitations. To that end, the present invention is directed to organic materials that have higher second order or third order susceptibilities than well known inorganic materials, and which are extremely easy to process because such compounds do not require electric poling or the preparation of large single crystals.

SUMMARY OF THE INVENTION

The present invention is directed to the compound 4-[4-(2R)-2-cyano-7-(4'-pentyloxy-4-biphenylcarbonyloxy)phenylheptylidene)phenylcarbonyloxy]benzaldehyde and the compound (12-hydroxy-5,7-dodecadiynyl) 4'-[(4'-pentyloxy-4-biphenyl)carbonyloxy]-4-biphenylcarboxylate, a hydroxylated aromatic diacetylene and its polymeric form. The present invention is also directed to a method for doubling the frequency of light by directing a light beam through crystals or acrystalline film of the compound 4-[4-(2R)-2-cyano-7-(4'-pentyloxy-4-biphenylcarbonyloxy)phenylheptylidene)phenylcarbonyloxy]benzaldehyde. Similarly, the invention is directed to a method for tripling the frequency of a light beam by directing a light beam through crystals or a crystalline film of the polymeric form of the compound (12-hydroxy-5,7-dodecadiynyl) 4'-[(4'-pentyloxy-4-biphenyl)carbonyloxy]-4-biphenylcarboxylate.

DETAILED DESCRIPTION OF THE INVENTION

Figure 1:
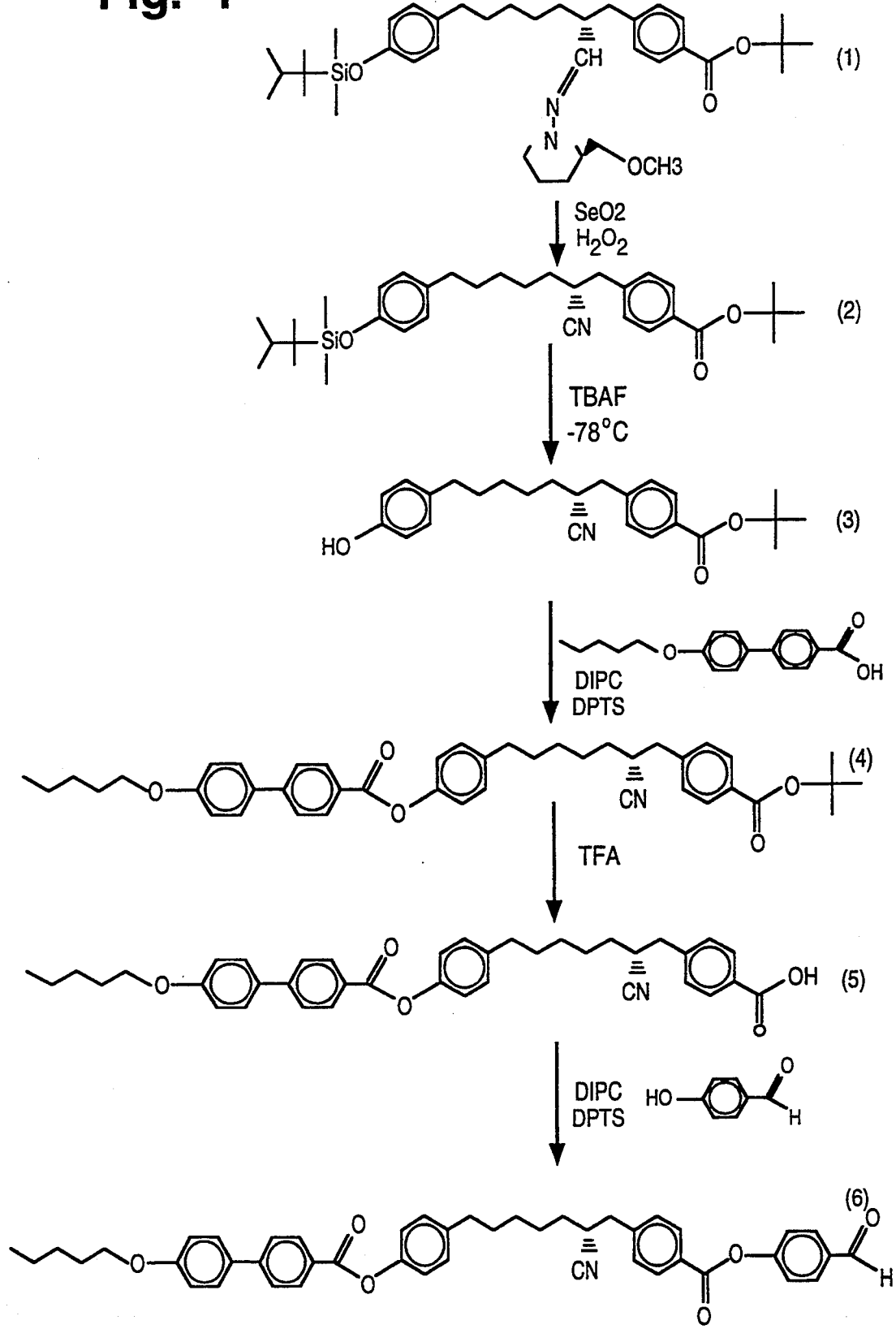
FIG. 1 shows the synthesis of 4-[4-(2R)-2-cyano-7-(4'-pentyloxy-4-biphenylcarbonyloxy)phenylheptylidene)phenylcarbonyloxy]benzaldehyde.

The present invention is directed to organic materials having nonlinear optical properties. One organic material of the present invention forms colorless crystals with a second order nonlinear optical susceptibility greater than $5 \times 10^{-7}$ esu. This compound has the ability to double the frequency of light. Another organic material, a polymer of (12-hydroxy-5,7-dodecadiynyl) 4'-[(4'-pentyloxy-4-biphenyl)carbonyloxy]-4-biphenylcarboxylate, has the ability to triple the frequency of light. This polymer may be generally characterized as a hydroxylated aromatic polydiacetylene.

Lasers produce light at a variety of different wavelengths in the visible, infrared and ultraviolet regions of the electromagnetic spectrum. However, a particular laser emits light at a characteristic wavelength. Thus, for example, a carbon dioxide laser emits light at a wavelength of 10.6 microns. A dye laser is tunable from 0.4 to 1 micron. See, for example, *Kirk-Othmer Concise Encyclopedia of Chemical Technology*, John Wiley and Sons, Inc., New York, pp. 685–685 (1985).

Owing to their exceptional nonlinear optical properties, the organic materials of the present invention can act to double or triple the frequency of laser light, depending on the material used. Thus, for example, an infrared laser beam is converted into green light at exactly twice the frequency when the laser beam traverses crystals or a crystalline film of 4-[4-(2R)-2-cyano-7-(4'-pentyloxy-4-biphenylcarbonyloxy)phenylcarbonyloxy]benzaldehyde.

An active crystalline film of 4-[4-(2R)-2-cyano-7-(4'-pentyloxy-4-biphenylcarbonyloxy)phenylheptylidene)phenylcarbonyloxy]benzaldehyde is formed spontaneously, i.e., without electric poling. When the crystalline film is composed of 4-[4-(2R)-2-cyano-7-(4'-pentyloxy-4-biphenylcarbonyloxy)phenylheptylidene)phenylcarbonyloxy]benzaldehyde, the crystalline phase consists of long flat crystals aligned along a common direction over macroscopic distances. Thus, formation of the active phase does not require exposure of the material to an external electric field as necessary in other systems that show nonlinear optical properties. As used herein, the term "active phase" shall mean the state of the organic material in which the material shows nonlinear optical properties.

The compound 4-[4-(2R)-2-cyano-7-(4'-pentyloxy-4-biphenylcarbonyloxy)phenylheptylidene)phenylcarbonyloxy]benzaldehyde must crystallize into a specific crystal structure in order to have nonlinear optical activity. The active phase is obtained by heating the compound to a temperature in the range of about 115° to about 120° C. and then cooling to allow crystals to form. If the compound is heated above this temperature range, very few, if any, active crystals form during cooling.

In one aspect, the invention is directed to the compound 4-[4-(2R)-2-cyano-7-(4'-pentyloxy-4-biphenylcarbonyloxy)phenylcarbonyloxy]benzaldehyde. This molecule has oligomeric dimensions, it is chiral and has a molar mass of 647. At high temperatures it forms liquid crystalline phases, including a cholesteric phase and blue phases. A very interesting feature of these crystals is their self-alignment over macroscopic distances, which results in the formation of transparent thin films. These films exhibit remarkably high second order nonlinear optical susceptibilities.

Its nonlinear optical properties are associated with a crystalline phase which forms near 115° C. and remains stable at room temperature. Three to six millimeter monodomains of aligned crystals form during crystallization from the cholesteric phase to a crystalline solid. Exposure of this material to electric or magnetic fields had no effect in biasing the crystal orientation.

One specific exceptional property of this compound is a high second order nonlinear optical susceptibility in bulk samples (not monolayers) which is higher than benchmark materials, such as lithium niobate ($\chi^{(2)} \sim 1.5 \times 10^{-7}$ esu).

The material is also colorless, a very important property when combined with nonlinear optical behavior since it implies that this compound would not extensively absorb light with visible wavelengths, and thus should be suitable to double many frequencies.

The present invention also provides an organic material, (12-hydroxy-5,7-dodecadiynyl) 4'-[(4'-pentyloxy-4-biphenyl)carbonyloxy]-4-biphenylcarboxylate, that will triple the frequency of light when the material is in its polymeric form. As used herein the name "(12-hydroxy-5,7-dodecadiynyl) 4'-[(4'-pentyloxy-4-biphenyl)carbonyloxy]-4-biphenylcarboxylate" shall mean the compound synthesized by the method of Synthesis 2 [compound (8)] of the Examples. The polymeric organic material has the advantage that it is generally resistant to laser damage. For example, the polymeric organic material may be exposed to 432,000 twenty nanosecond pulses at 20 Hz (1064 nm wavelength) without any evidence of damage to the organic material. The ability to resist damage to laser light is important in photonic applications. Examples of photonic applications in which a compound that doubles or triples the frequency of light might be useful include, but are not limited to, electrooptic modulators of light polarization, Mach-Zehnder interferometers, optical switches, optical interconnectors, frequency doublers for high power lasers, active waveguides, optical memory storage devices, optical computing devices, and all optical guided wave devices such as nonlinear directional couplers and nonlinear Bragg reflectors.

The compound (12-hydroxy-5,7-dodecadiynyl) 4'-[(4'-pentyloxy-4-biphenyl)carbonyloxy]-4-biphenylcarboxylate can self-assemble to form highly oriented thin films. These films can polymerize spontaneously or after exposure to ultraviolet light. It is the polymeric form of this compound that shows excellent nonlinear optical properties.

The compound (12-hydroxy-5,7-dodecadiynyl) 4'-[(4'-pentyloxy-4-biphenyl)carbonyloxy]-4-biphenylcarboxylate is colorless. However, the polymer of this compound is blue. When the polymeric material is heated or exposed to organic liquids, it may turn red or orange, depending on the temperature, with orange predominating at higher temperatures. However, these color changes do not affect the material's ability to triple the frequency of light. For example, when the blue polymeric material is heated from room temperature to about 70° C. or placed in an organic liquid, the material turns red and will return to blue upon cooling. However, when the blue material is heated above 100° C., the material turns orange and will not return to blue when cooled. The polymer of the compound (12-hydroxy-5,7-dodecadiynyl) 4'-[(4'-pentyloxy-4-biphenyl)carbonyloxy]-4-biphenylcarboxylate forms spontaneously when the solvent that is part of the reaction mixture is removed. Alternatively, the reaction mixture may be allowed to stand and the polymeric compound may be obtained as a blue precipitate. To obtain a crystalline film of the compounds that have nonlinear optical properties, the film may be cast from a solution by evaporating the solvent such as chloroform.

Part of the light intensity of a particular frequency may be doubled or tripled by the organic materials of the present invention by placing the organic materials in the path of the light. Part of that light which is emitted from the organic materials, when the material is in the active phase, will have a frequency that is double or triple the frequency of the light that entered the organic material. In the case of the compound that doubles the frequency of light, the active phase comprises cystals of the compound made under the conditions described above. In the case of the compound that triples the frequency of light, the active phase is the polymeric form. If it is desired to double the frequency of light, the compound 4-[4-(2R)-2-cyano-7-(4'-pentyloxy-4-biphenylcarbonyloxy)phenylheptylidene)phenylcarbonyloxy]benzaldehyde may be used. If it is desired to triple the frequency of light, the compound (12-hydroxy-5,7-dodecadiynyl) 4'-[(4'-pentyloxy-4-biphenyl)carbonyloxy]-4-biphenylcarboxylate may be used.

Compounds that have nonlinear optical properties, particualrly second order nonlinear optical properties, may also demonstrate the Pockels Effect, which has been called the linear electrooptical effect. The Pockels effect is a phenomenon whereby the index of refraction of a compound changes when an electric field is applied to the compound. Generally, the change in the refractive index of the compound is proportional to the $\chi^{(2)}$ value of the material.

The following examples further illustrate the invention and are not to be construed as limiting of the specification and claims in any way.

EXAMPLES

Synthesis 1 below shows the synthesis of 4-[4-(2R)-2-cyano-7-(4'-pentyloxy-4-biphenylcarbonyloxy)phenylheptylidene)phenylcarbonyloxy]benzaldehyde. FIG. 1 shows the synthesis in diagrammatic form.

Synthesis 1 4-[4-(2R)-2-cyano-7-(4'-pentyloxy-4-biphenylcarbonyloxy)phenylheptylidene)phenylcarbonyloxy]benzaldehyde

Step 1 Tert-butyl 4-[(2R)-2-cyano-7-(4-dimethylhexylsilyloxyphenyl)heptylidene]benzoate To a stirred suspension of (2R)-2-methoxymethyl-1-[(2R)-3-(4-tert-butyloxycarbonylphenyl)-2-(pentamethylene-5-(4-dimethylhexylsilyloxyphenyl))-propylidenamino]pyrrolidine (1) (For the synthesis of (1) see Synthesis 1A below) (14.6 g, 22.4 mmol) and $SeO_2$ (2.0 g, 18 mmol) in 227 ml of methanol was added 30% $H_2O_2$ (7.3 ml) at once. After being stirred at room temperature for 30 minutes, the solution was transferred to a separatory funnel containing 700 ml of $CH_2Cl_2$. The combined organic layer was washed with brine water (600 ml), dried (MgSO$_4$) and then concentrated. The residue was purified by flash column chromatography using a mixture of petroleum ether and ethyl acetate (9:1) as eluent to give 10.7 g (89% yield) of the title compound as an oil.

MS (FAB): 535(M+);

$^1$H NMR (300 MHz, CDCl$_3$, TMS) δ 0.21 (S, 6H), 0.93 (S, 6H), 0.94 (d, J=6.8 Hz, 6H) 1.26–1.77 (m, 9H), 1.58 (S, 9H), 2.52 (t, J=7.8 Hz, 2H), 2.73–2.78 (m, 1H), 2.90–2.94 (m, 2H), 6.74 (d, J=8.3 Hz, 2H), 7.00 (d, J=8.4 Hz, 2H), 7.28 (d, J=82. Hz, 2H), 7.96 (d, J=8.2 Hz, 2H);

$^{13}$C NMR (75 MHz, CDCl$_3$) δ −2.47 (CH$_3$), 18.55 (CH$_3$), 20.13 (CH$_3$), 24.99 (C), 26.62 (CH$_2$), 28.16 (CH$_3$), 30.99 (CH$_2$), 31.64 (CH$_2$), 33.44 (CH), 34.11 (CH), 34.73 (CH$_2$), 38.22 (CH$_2$), 81.02 (C), 119.89 (CH), 121.35 (C), 128.82 (CH), 129.08 (CH), 129.83 (CH), 131.06 (C), 134.46 (C), 141.54 (C), 153.50 (C), 165.39(C);

Elemental Analysis: Calculated for (C$_{37}$H$_{45}$NO$_3$Si) (Mw=535.83): C,73.65; H,9.08; N,2.68. Found: C,73.66; H,9.15; N, 2.67.

Figure 2:
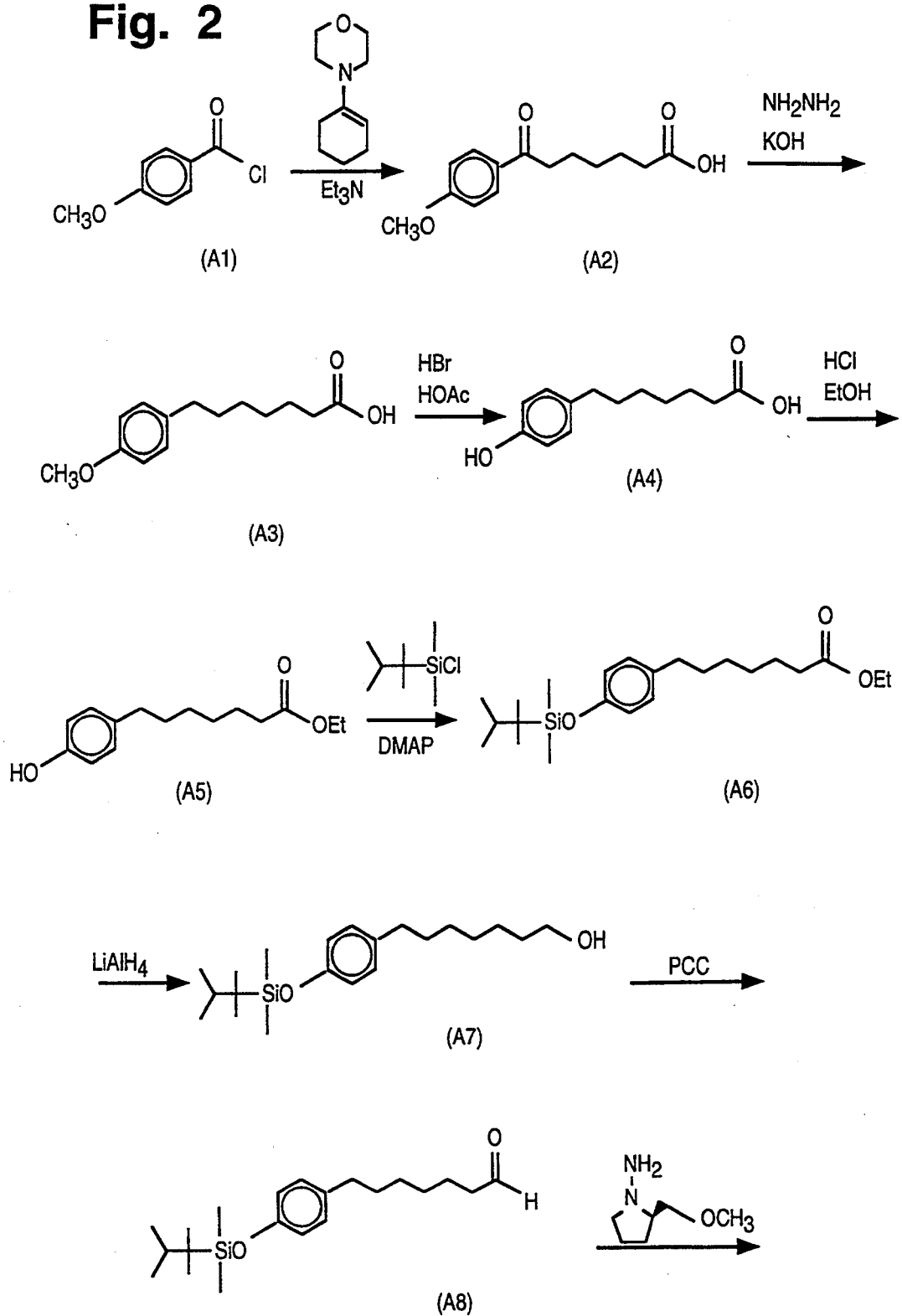
FIG. 2 shows the synthesis of (2R)-2-methoxymethyl-1-[(2R)-3-(4-tert-butyloxycarbonylphenyl)-2-(pentamethylene-5-(4-dimethylhexylsilyloxyphenyl))-propylidenamino]pyrrolidine.
Figure 2:
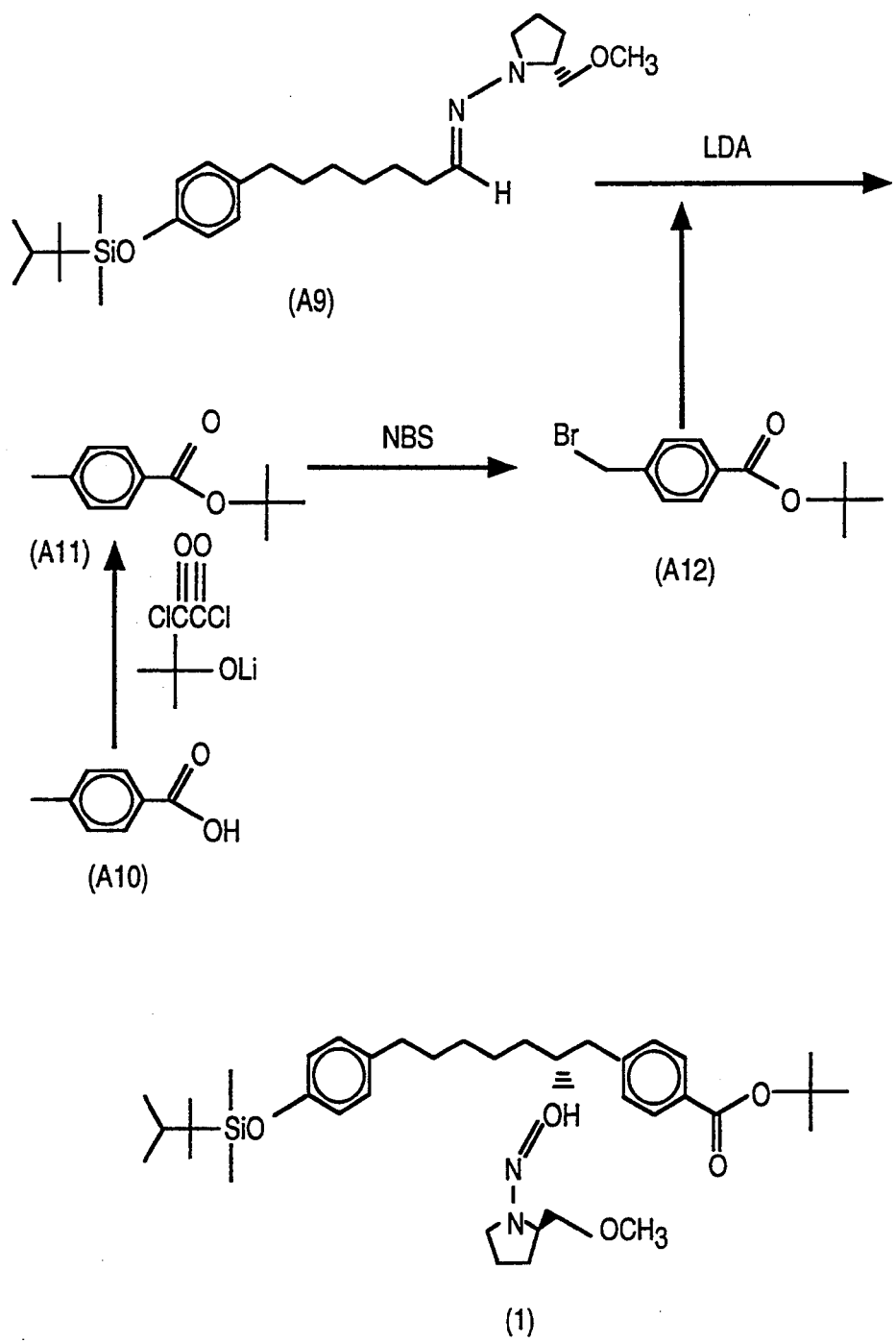

Synthesis 1A (2R)-2-Methoxymethyl-1-[(2R)-3-(4-tert-butyloxycarbonylphenyl)-2-(pentamethylene-5-(4-dimethylthexylsilyloxyphenyl))propylidenamino]pyrrolidine (FIG. 2 shows the synthesis in diagrammatic form.)

Step 1A 7-(4-Methoxyphenyl)-7-oxoheptanoic acid

A dry, three-neck, three liter flask fitted with a 500 ml addition funnel, mechanical stirrer, and Claisen adapter connected to an argon inlet and thermometer, was purged with argon and charged with dry and ethanol free chloroform (150 ml). The addition funnel was charged with p-anisoyl chloride (100 g, 58.6 mole) in CHCl$_3$ (120 ml). To the flask was added dry Et$_3$N (1.1 equiv.), and 1-morpholino-1-cyclohexene (1.05 equiv.). The solution of p-anisoyl chloride was added over 30 minutes and external cooling was applied as needed to maintain an internal temperature of less than 35° C. An orange to deep red color developed along with a precipitate as stirring at room temperature was maintained for 12 hours. The solution was divided into 300 ml portions and each extracted with brine (1×150 ml) and water (1×150 ml). The organic layers were combined, dried (MgSO$_4$) and concentrated by rotary evaporation (bath temperature 45° C.).

The crude oil was placed in a three liter, single-neck flask along with dioxane (375 ml), concentrated HCl (150 ml), glacial acetic acid (300 ml) and water (450 ml). The mixture was refluxed vigorously for 20 hours. At this point, the reaction's progress was monitored by TLC (developed with 25% acetone in petroleum ether). The desired arylketo acid gives only a baseline TLC spot under these eluting conditions, while the starting enamine and intermediate 1,3-diketone have R$_f$ values of 0.15 and 0.38, respectively. Refluxing was continued as necessary up to a total time of 30 hours. The dark solution was cooled, placed in the refrigerator overnight, and the resulting solid was collected by suction filtration. The solid was then taken up in hot 1N sodium hydroxide solution (600 ml) to ensure complete cleavage of the 1,3-diketone. After cooling, the solution was acidified with concentrated HCl and the white solid collected and dried. The resulting arylketo acid was of sufficient purity to be used in the next step, although analytically pure material may be obtained by recrystallization from water.

MW: 250.28 (C$_{14}$H$_{18}$O$_4$)
Yield: 85.7 g (58.4%)
mp: 130° C.

MS (70 eV): 250(7, M+), 163(23), 151(44), 150(100), 136(43), 135(100).

$^1$HMNR (300 MHz, d$_6$-Me$_2$SO, TMS): δ 1.32–1.34(m, 2H); 1.50–1.62(m, 4H); 2.20(t, J=7.3 Hz, 2H); 2.94(t, J=7.2 Hz, 2H); 3.84(s, 3H), 7.03(d, J=8.7 hz, 2H), 7.94(d, J=8.7 Hz, 2H), 12.02(br s, 1H).

$^{13}$C-NMR (75 MHz, CDCl$_3$): δ 23.71 (CH$_2$); 24.39(CH$_2$); 28.25(CH$_2$); 33.57(CH$_2$); 37.32(CH$_2$); 55.40(CH$_3$); 113.73(CH); 129.01(CH); 130.08(CH); 131.25(CH); 162.91(C); 174.39(C); 198.19(C).

Elemental Analysis: Calculated: C,67.18; H, 7.20. Found: C,67.46; H,7.22.

Step 2A 7-(4-Methoxyphenyl)heptanoic acid

A single-neck, 100-ml flask fitted with a reflux condenser, stir bar and drying tube was charged with 7-(4-methoxyphenyl)-7-oxoheptanoic acid (A2) (3.1 g, 12.4 mmole), diethylene glycol (15 ml), and 85% hydrazine hydrate (5 ml). The mixture was heated for 3.5 hours in an oil bath maintained at 120° C. The flask was then cooled to 60° C. and an aspirator vacuum (10 mm) was applied for 2 hours during which time the bath temperature was slowly raised to 130° C. The temperature was again lowered and potassium hydroxide pellets (3.9 g) were added. The reaction mixture was heated slowly to 155° C. over a period of 1 hour and this temperature was maintained for an additional 2 hours. During this time, steady foaming of the solution occurred. After cooling to room temperature, the solid was stirred with water (20 ml) and acidified with concentrated HCl. The residue was collected after refrigeration and washed with plenty of water. The remaining solid was taken up in acetone and the insoluble material filtered off. The acetone solution was concentrated leaving the title compound (A3).

MW: 236.30
Yield: 38.33 (76.6%)

MS (70 eV): 236(19, M+), 122(9), 121(100).

$^1$H-NMR (300 MHz, CDCl$_3$, TMS): δ 1.33–1.36(m, 4H); 1.56–1.66(m, 4H); 2.34(t, J=7.0 Hz, 2H); 2.54(t, J=7.4 Hz, 2H); 3.79(s, 3H); 6.82(d, J=8.4 Hz, 2H); 7.08(d, J=8.4 Hz, 2H).

$^{13}$C-NMR (75 MHz, CDCl$_3$): δ 24.56(CH$_2$); 28.78(CH$_2$); 28.86(CH$_2$); 31.47(CH$_2$); 34.01(CH$_2$); 34.88(CH$_2$); 55.21(CH$_3$); 113.61(CH); 129.20(CH); 134.70(C); 157.56(C); 180.25(C).

Step 3A 7-(4-Hydroxyphenyl)heptanoic acid

A 500 ml single-neck flask was charged with 7-(4-methoxyphenyl)heptanoic acid (A3) (20.0 g, 90 mmole), freshly distilled 48% hydrobromic acid (80 ml), and glacial acetic acid (40 ml). The mixture was heated to reflux by immersing the flask in an oil bath regulated at 140° C. for 3.5 hours. At the end of this time, water (80 ml) was added, the flask was cooled to room temperature, and placed in the refrigerator overnight. The resulting solid, 7-(4-hydroxyphenyl)heptanoic acid, was collected by suction filtration, washed with water (2×80 ml), and dried in vacuo. The product was of sufficient purity to be used in the next step.

MW: 222.28
Yield: 85%

MS (70 eV): 222(29, M+), 204(3), 176(4), 133(3), 108(9), 107(100).

¹H-NMR (300 MHz, d₆-Me₂SO, TMS): δ 1.25–1.27(br s, 4H); 1.45–1.48(br s, 4H); 2.10(t, J=7.3 Hz, 2H); 2.13(t, J=7.8 Hz, 2H); 6.64(d, J=8.3 Hz, 2H); 6.95(d, J=8.3 Hz, 2H); 9.09(s, 1H); 11.98(br s, 1H).

¹³C-NMR (75 MHZ, d₆-Me₂SO, TMS): δ 24.41(CH₂); 28.29(CH₂); 28.34(CH₂); 31.17(CH₂); 33.56(CH₂); 34.20(CH₂); 114.86(C); 128.90(CH); 132.23(C); 155.13(C); 174.41(C).

Step 4A Ethyl 7-(4-hydroxyphenyl)heptanoate

A 300 ml flask fitted with a Claisen adapter connected to a gas inlet and a drying tube was charged with freshly opened ethanol (100 g). The flask was placed in a water bath to provide external cooling and anhydrous HCl gas was bubbled through the ethanol. When the weight of the flask increased by 35 g, gas flow was stopped affording a 25% (by wt.) solution of HCl in ethanol.

A 500 ml single-neck flask was charged with 7-(4-hydroxyphenyl)heptanoic acid (A4) (17.7 g, 79.7 mmole), 35 ml of the 25% HCl solution, and ethanol (90 ml). The flask was immersed in an oil bath and refluxed 4.5 hours. After cooling to room temperature, the contents were poured onto ice water (750 ml) and 375 ml of saturated sodium bicarbonate were added. The mixture was extracted with ether (3×225 ml), the combined organic layers dried (MgSO₄), and concentrated by rotary evaporation (2–4 hours at 45° C.). The resulting oil, Ethyl 7-(4-hydroxyphenyl)heptanoate, was of sufficient purity to be used in the next step.

MW: 250.33
Yield 98%

¹H-NMR (300 MHz, d₆-Me₂SO, TMS): δ 1.17(t, J=7.1 Hz, 3H); 1.19–1.27(m, 4H); 1.48(br s, 4H); 2.25(t, J=7.3 HZ, 2H); 2.43(t, J=7.6 Hz, 2H); 4.03(q, J=7.0 Hz, 2H); 6.65(d, J=8.2 Hz, 2H); 6.95(d, J-8.2 Hz, 2H); 9.2(br s, 1H).

¹³C-NMR (75 MHZ, CDCl₃, TMS): δ 14.20(CH₃); 24.89(CH₂); 28.95(CH₂); 31.47(CH₂); 34.41(CH₂); 34.92(CH₃); 60.49(CH₂); 115.08(CH); 129.31(CH); 134.50(C); 153.80(C); 174.53(C).

Step 5A Ethyl 7-(4-dimethylthexylsilyloxyphenyl)heptanoate

A one-liter, single-neck flash containing ethyl 7-(4-hydroxyphenyl)heptanoate (A5) (28.0 g, 112 mmole) was fitted with a Claisen adapter connected to a septum and drying tube. The flask was charged with dry CH₂Cl₂ (180 ml), dimethylaminopyridine (3.2 g, 26 mmole), and dry triethylamine (18 ml, 129 mmole). Dimethylthexylsilyl chloride (24.6 ml, 125 mmole) was then added dropwise via syringe at room temperature. The mixture was stirred overnight during which time a white precipitate formed. The next day, pentane (180 ml) was added and the solid was removed by filtration through a 40 g pad of silica gel. The silica gel was washed with 200 ml of a 1:1 mixutre of CH₂Cl₂: pentane and the solvent was exaporated. The resulting pale yellow oil, Ethyl 7-(4-dimethylthexylsilyloxyphenyl)-heptanoate, could be purified either by column chromatography (silica gel, 50% CH₂Cl₂ in petroleum ether) or by fractional distillation under vacuum through a 3 cm Vigreaux column.

MW: 392.62
Yield: 93% after distillation
bp: 185°–195° C. @ 0.15 mm

¹H-NMR (300 MHz, CDCl₃, TMS): δ 0.20(s, 6H); 0.94(s, 6H); 0.94(d, J=6.8 Hz, 6H); 1.25(t, J=7.2 Hz, 3H); 1.33(br s, 4H); 1.54–1.61(m, 4H); 1.59(m, 1H); 2.28(t, J=7.6 Hz, 2H); 2.52(t, J=7.8 Hz, 2H); 4.11(q, J=7.2 Hz, 2H); 6.72(d, J=8.4 Hz, 2H); 7.00(d, J=8.4 Hz, 2H).

¹³C-NMR (75 MHz, CDCl₃, TMS): δ −2.44(CH₃); 14.27(CH₃); 18.58(CH₃); 20.18(CH₃); 24.92(CH₂); 25.02(C); 28.51(CH₂); 29.00(CH₂); 31.44(CH₂); 34.17(CH); 34.36(CH₂); 35.03(CH₂); 60.15(CH₂); 119.8(CH); 129.12(CH); 135.25(C); 153.33(C); 173.82(C).

Step 6A
7-(4-Dimethylthexylsilyloxyphenyl)heptan-1-ol

A dry, three-neck, one-liter flask fitted with reflux condenser, mechanical stirrer and argon inlet was flushed with argon and charged with lithium aluminum hydride (3.0 g, 70 mmole). Using a cannula, dry ether (180 ml) was added and the addition funnel was charged with a solution of ethyl 7-(4-dimethylthexylsilyloxyphenyl)heptanoate (A6) (36.9 g, 93.9 mmole) in ether (170 ml). The solution in the addition funnel was added dropwise to the rapidly stirred suspension of LiAlH₄ at a rate to maintain gentle reflux (the addition required about 45 minutes). At the end of this time, the mixutre was briefly refluxed by external heating and then cooled to 0° C. Cautiously, water (3.0 ml), 15% KOH solution (3.0 ml) and water (9 ml) were added in succession. The mixture was heated to reflux once again to complete the hydrolysis (10 minutes). After cooling white solids were removed by suction filtration through a fritted glass funnel and thoroughly washed with ether. The solids were returned to the original flask and refluxed with ether (150 ml). The solids were removed and the ether washings were combined and dried over K₂CO₃. The solvent removed by rotary evaporation (2 hours at 45° C.) affording the alcohol 7-(4-dimethylthexylsilyloxyphenyl)heptan-1-ol of sufficient purity to be used in the next step.

MW: 350.6
Yield: 98%

¹H-NMR (300 MHz, CDCl₃, TMS): δ 0.21(s, 6H), 0.94(s, 6H); 0.04(d, J=6.8 Hz, 6H); 1.34(br s, 6H); 1.56(br s, 4H); 1.72(m, 1H); 2.52(t, J=7.9 Hz, 2H); 3.63(t, J=6.6 Hz, 2H); 6.73(d, J=8.4 Hz, 2H); 7.01 (d, J=8.4 Hz, 2H).

¹³C-NMR (75 MHz, CDCl₃): δ −2.47(CH₃); 18.57(CH₃); 20.15(CH₃); 24.97(C); 25.65(CH₂); 29.18(CH₂); 29.28(CH₂); 31.58(CH₂); 32.73(CH₂); 34.12(CH); 35.10(CH₂); 63.00(CH₂); 119.77(CH); 129.11(CH); 135.36(C); 153.28(C).

Step 7A 7-(4-Dimethylthexylsilyloxyphenyl)heptanal

A dry, 250 ml single-neck flash containing an efficient stir bar and fitted with a Claisen adapter connected to a drying tube and septum was charged with pyridinium chlorochromate (9.58 g, 44.4 mmole) and dry CH₂Cl₂ (64 ml). The suspension was stirred rapidly as a solution of 7-(4-dimethylthexylsilyloxyphenyl)heptan-1-ol (A7) (10.4 g, 29.7 mmole) in CH₂Cl₂(10.0 ml) was added in one portion. Rapid stirring was continued for 2 hours at room temperature. At this time, dry ether (65 ml) was added and the dark mixture was allowed to stand for 10 minutes. The liquid was decanted into a flask and the tar-like residue was washed with dry ether (3×30 ml) using thorough mechanical stirring to mix the tar. The decanted liquids were combined and filtered through a 5 g pad of Celite ®, which was then washed with ether (1×50 ml), (Celite ® is a filtering aid that may be purchased from The Aldrich Chemical Company of Milwaukee, Wis.). The solvent from the filtrate was removed leaving a dark colored oil. The residue was immediately subjected to flash column chromatography (silica gel, 9% ethyl acetate in petroleum ether) affording a colorless liquid, 7-(4-dimethylthexylsilyloxyphenyl)heptanal.

MW: 348.58
Yield: 77%

$^1$H-NMR (300 MHz, CDCl$_3$, TMS): δ 0.21(s, 6H); 0.94 (s, 6H); 0.94(d, J=6.9 Hz, 5H); 1.33(br s, 4H); 1.55–1.75(m, 5H); 2.39(td, J$_{1,2}$=1.5 Hz, J$_{2,3}$=7.3 Hz, 2H); 2.52(t, J=7.9 Hz, 2H); 6.73(d, J=8.4 Hz, 2H); 7.00(d, J=8.4 Hz, 2H); 9.74(s, 1H).

$^{13}$C-NMR(75 MHz, CDCl$_3$, TMS): δ −2.45(CH$_3$); 18.57(CH$_3$); 20.15(CH$_3$); 21.98(CH$_2$); 24.97(C); 28.90(CH$_2$); 28.99(CH$_2$); 31.41(CH$_2$); 34.13(CH); 35.01(CH$_2$): 48.83(CH$_2$); 119.80(CH); 129.12(CH); 135.14(C); 153.35(C); 202.75(C).

Step 8A
(R)-1-[7-(4-Dimethylthexylsilyloxyphenyl)heptylidenamino]-2-methoxymethylpyrrolidine A dry, 250 ml, single-neck flask fitted with a Claisen adapter connected to a septum and drying tube was charged with RAMP (4.8 g, 36.9 mmole)[RAMP is (R)-(+)-1-amino-2-(methoxymethyl)pyrolidine, from The Aldrich Chemical Company, Milwaukee, Wis.]. The flask was cooled to 0° C. and 7-(4-dimethylthexylsilyloxyphenyl)heptanal (A8) (11.7 g, 33.5 mmole) was added dropwide. The contents were stirred at room temperature for 2 hours. At this point, ether (60 ml) was added along with Na$_2$SO$_4$ (23 g) and the mixture was stirred 30 minutes further. The solution was decanted into a flask and the drying agent washed thoroughly with several portions of ether. After the solvent was removed by rotary evaporation, the residue was purified by column chromatography (silica gel, eluted with 20% ethyl acetate in petroleum ether) affording a colorless oil, (R)-1-[7-(4-dimethylthexylsilyloxyphenyl)heptylidenamino]-2-methoxymethylpyrrolidine.

MW: 460.75 (C$_{27}$H$_{48}$N$_2$O$_2$Si)
Yield: 96%

$^1$H-NMR (300 MHz, CDCl$_3$, TMS): δ 0.21 (s, 6H); 0.94(s, 6H); 0.94(d, J=6.9 Hz, 6H); 1.34(br s, 4H); 1.46(m, 2H); 1.57(m, 2H); 1.70–1.94(m, 5H); 2.18(td, J$_{1,2}$=5.6 HZ, J$_{2,3}$=7.8 Hz, 2H); 2.52(t, J=7.4 Hz, 2H); 2.70(m, 1H); 3.30–3.58(m, 4H); 3.37(s,3H); 6.64(t, J=5.6 Hz, 1H); 6.73(d, J=8.4 Hz, 2H); 7.01(d, J=8.4 Hz, 2H).

$^{13}$C-NMR (75 MHz, CDCl$_3$, TMS): δ −2.46(CH$_3$); 18.56(CH$_3$); 20.15(CH$_4$); 22.16(CH$_2$); 24.97(C); 26.56(CH$_2$); 27.79(CH$_2$); 29.08(CH$_2$); 31.57(CH$_2$); 33.12(CH$_2$); 34.12(CH); 35.07(CH$_2$); 50.54(CH$_2$); 59.19(CH$_3$); 63.49(CH); 74.86(CH$_2$); 119.74(CH); 129.10(CH); 135.356(C); 139.55(CH); 153.24(C).

Elemental Analysis: Calculated: C,70.38; H,10.50; N,6.08 Found: C,70.47; H,10.55; N,6.18.

Step 9A
(2R)-2-Methoxymethyl-1-[(2R)-3-(4-tert-butyloxycarbonylphenyl)-2-(pentamethylene-5-(4-dimethylthexylsilyloxyphenyl)propylidenamino]pyrrolidine A dry, 250 ml, single-neck flask containing a glass-coated stir bar was fitted with a Claisen adapter connected to an argon inlet. The flask was flame dried under a vacuum and thoroughly flushed with argon. The flask cooled to −78° C. and was charged with dry THF (33 ml), freshly distilled diisopropylamine (2.71 ml, 19.3 mmole), and a solution of 1.55N n-butyllithium (10.8 ml, 16.7 mmole) was added dropwise. After stirring 15 minutes, a solution of (R)-1-[7-(4-dimethylthexylsilyloxyphenyl)heptylidenamino]-2-methoxymethylpyrrolidine (A9) (7.4 g, 10.1 mmole) in THF (12.2 ml) was cooled to −78° C. and added slowly, via a cannula, to the solution. Stirring at this temperature continued for 1 hour and then the dry ice was removed from the cooling bath, allowing the temperature to rise to −5° C. over the next 2.5 hours. Upon reaching −5° C., the dry ice bath was replaced with a ice/salt bath regulated between −10° to −5° C. The mixture was stirred at this temperature for 3 hours during which time a pale yellow, homogeneous solution developed. At this point, the flask was cooled to −95° C. (methanol/liquid nitrogen) and after allowing sufficient time for complete temperature equilibration, a solution of tert-butyl 4-(α-bromotoluate) (A12) [For the synthesis of (A12), see steps 10A and 11A below.], 5.23 g, 19.3 mmole) in THF (8.8 ml) was added dropwise via a cannula. A bright orange color developed as (A12) was added. Stirring at −95° C. was continued 1 hour during which time the color faded to a light orange-yellow. The temperature was allowed to gradually warm to −20° C. over the next 2 hours and the reaction mixture was then transferred to a separatory funnel along with ether (300 ml). The solution was washed with 0.5M sodium bicarbonate solution (1×120 ml) and the organic phase was dried over MgSO$_4$. The drying agent was then removed by vacuum filtration followed by concentration of the solution by rotary evaporation. The residue was purified by flash column chromatography by using dichloromethane as an eluent. When the product started to come out from the column, the eluent was changed to a mixture of dichloromethane and diethyl ether (11:1) to afford a colorless oil, (2R)-2-methoxymethyl-1-[(2R)-3-(4-tert-butyloxycarbonylphenyl)-2-(pentamethylene-5-(4-dimethylthexylsilyloxyphenyl))propylidenamino]pyrrolidine (1).

MW: 650:98 (C$_{39}$H$_{62}$N$_2$O$_4$Si)
Yield: 70%

$^1$H-NMR (300 MHz, CDCl$_3$, TMS): δ 0.2(s, 6H); 0.93(s, 6H); 0.93(d, J=6.7 Hz, 6H); 1.26–1.37(m, 6H), 1.50–1.58(m, 2H); 1.58(2, 9H); 1.67–1.92(m, 5H); 2.49(t, J=8.0 Hz, 2H); 2.53–2.82(m, 4H); 3.30–3.49(m, 4H); 3.35(s, 3H); 6.42(d, J=6.5 Hz, 1H); 6.72(d, J=8.5 Hz, 2H); 6.98(d, J=8.5 Hz, 2H); 7.20(d, J=8.2 Hz, 2H); 7.87(d, J=8.2 Hz, 2H).

$^{13}$C-NMR (75 MHz, CDCl$_3$): δ 2.45(CH$_3$); 18.57(CH$_3$); 20.16(CH$_3$); 22.06(CH$_2$); 24.97(C); 26.43(CH$_2$); 26.82(CH$_2$); 28.20(CH$_3$); 29.28(CH$_2$); 31.57(CH$_2$); 33.07(CH$_2$); 34.14(CH); 35.07(CH$_2$); 40.09(CH$_2$); 43.68(CH); 50.31(CH$_2$); 59.16(CH$_3$); 63.35(CH); 74.65(CH$_2$); 80.61(C); 119.75(CH); 129.10(CH); 129.14(CH); 129.25(CH); 129.60(C); 135.32(C); 141.25(CH); 145.48(C); 153.27(C); 164.82(C).

Elemental Analysis: Calcuated: C,71.95; H,9.60; N,4.30. Found: C,71.97; H,9.55; N,4.30.

Step 10A Tert-butyl-4-toluate

A 250 ml round bottomed flask fitted with a reflux condenser and Calisen adapter attached with a rubber septum and drying tube was charged with 20 g of p-toluic acid, 80 ml of freshly distilled methylenechloride and 17.8 ml of oxalyl chloride. One drop of dimethylformamide was then added and the solution was refluxed 1.5 hours. The solvent was removed by rotary evaporation and the residue was taken up in 100 ml of diethyl ether.

A 1 L three-neck flask fitted with a reflux condenser, rubber septum, addition funnel and argon inlet was charged with 200 ml of t-butanol. To the solution, n-butyl lithium (1.45N, 91.1 ml) was added dropwise using a water bath to prevent an excessive temperature rise. After stirring 30 minutes, the addition funnel was charged with p-toluoyl chloride, added dropwise. The reaction mixture was stirred overnight. At this point, the contents were transferred into a separatory funnel by using 250 ml of diethyl ether and the solution was washed with water (250 ml). The organic layer was then dried (MgSO$_4$) and concentrated by rotary evaporation. The crude product, tert-butyl-4-toluate, was purified by fractional distillation.

MW: 192.26
Yield 23.73 g
bp: 78°–79° C. @ 0.8 mm
$^1$H-NMR (300 NHz, CDCl$_3$) 1.60(s, 9H), 2.40(s, 3H), 7.21(d, J=8.2 Hz, 2H), 7.85(d, J=8.1 Hz, 2H).

Step 11A Tert-butyl-4-(α-bromotoluate)

A dry, two-liter, single-neck flask fitted with a Claisen adapter connected to a reflux condenser, drying tube and septum was charged with carbon tetrachloride (600 ml) and tert-butyl-4-toluate (A11) (108.3 g, 0.56 mole). The Claisen adapter was briefly removed and benzoyl peroxide (500 mg) and N-bromosuccinimide (100.3 g, 0.56 mole, 1.0 equiv.) were added. The flask was immersed in an oil bath at room temperature and the temperature was slowly raised to 90° C. Once this temperature was attained, a vigorous reaction ensued and the formation of succinimide was observed. Heating at reflux continued 45 minutes and the contents were cooled to room temperature. The mixture was divided into two equal portions, each being washed with saturated sodium bicarbonate (2×200 ml). The organic layers were combined, dried (MgSO$_4$), and concentrated leaving a colorless oil (100%-crude yield). The oil was taken up in pentane (715 ml) and placed in the refrigerator (−12° C.) overnight. The solid crystals were collected by suction, washed with cold pentane and air dried. The mother liquors were set aside and the crystals from the first crop were redissolved in pentane (235 ml) and refrigerated at −12° C. The crystals formed were collected, washed with cold pentane and dried to obtain 44.35 g. The mother liquors from the first and second crops were combined, concentrated, dissolved in pentane (350 ml), and crystallized by standing in the refrigerator. The resulting solid was collected, washed with cold pentane, and recrystallized from pentane (210 ml) to obtain 27.25 g of tert-butyl-4-(α-bromotoluate) (A12) of purity equal to that of the first batch described above.

MW: 271.15 (C$_{12}$H$_{15}$BrO$_2$)
Yield: 71.61 g (46.8%)
MS (70 eV): (2,M+), 217(42), 215(46), 191(28), 135(100), 57(86), 56(66).
$^1$H-NMR (300 MHz, CDCl$_3$, TMS): δ 1.59(s, 9H), 4.49(s, 2H); 7.42(d, J=8.1 Hz, 2H); 7.96(d, J=8.1 Hz, 2H).
$^{13}$C-NMR (75 MHz, CDCl$_3$): δ 28.08(CH$_3$); 32.36(CH$_2$); 81.13(C); 128.77(CH); 129.80(CH); 131.84(C); 142.00(C); 165.05(C).
Elemental Analysis: Calculated: C,53.15; H,5.58. Found: C,53.37; H,5.75.

Step 2 Tert-butyl 4-[(2R)-2-cyano-7-(4-hydroxyphenyl)heptylidene]benzoate

A solution of tert-butyl 4-[(2R)-2-cyano-7-(4-dimethylthexylsilyloxyphenyl) heptylidene] benzoate (2) in dry tetrahydrofuran (17 ml) was stirred at room temperature for 5 minutes to form a homogeneous solution and then cooled to −78° C. under a nitrogen atmosphere. With vigorous stirring, TBAF (TBAF is tetra-n-butylammonium fluoride) (6.1 ml of a 1.0N solution in tetrahydrofuran) was added dropwise via a cannula. After being stirred for 2 hours at −78° C., 1.5 ml of TBAF solution was further added and stirring was continued for 1 more hour. At this point, the reaction mixture was quenched with a solution of acetic acid (340 mg) in diethyl ether (34 ml) at −78° C. The contents were poured into 300 ml of H$_2$O, and extracted with diethyl ether (2×150 ml), followed by washing with brine water (150 ml). The organic layer was dried (MgSO$_4$) and concentrated. This compound was pure enough to be used for the next step without purification and was obtained in about a 100% yield.

$^1$H NMR (300 MHz, CDCl$_3$, TMS) δ 1.31–1.86 (m, 8H), 1.59 (s, 9H), 2.53 (t, J=7.7 Hz, 2H), 2.55 (m, 1H), 2.90–2.95 (m, 2H), 6.76 (d, J=8.3 Hz, 2H), 7.03 (d, J=8.4 Hz, 2H), 7.28 (d, J=8.3 Hz, 2H), 7.97 (d, J=8.2 Hz, 2H).

Step 3 Tert-butyl 4-[(2R)-2-cyano-7-(4-((4-pentyloxy-4'-biphenyl)carbonyloxy)phenyl)heptylidene]benzoate To a suspension of tert-butyl 4-[(2R)-2-cyano-7-(4-hydroxyphenyl)heptylidene]benzoate (3) (1.6 g, 4.1 mmol), 4'-pentyloxy-4-biphenylcarboxylic acid (1.15 g, 3.9 mmol){4'-pentyloxy-4-biphenylcarboxylic acid may be made by the following procedure: 4'-hydroxy-4-biphenylcarboxylic acid (9.5 g, 42.4 mmole) and KOH (4.8 g, 84.8 mmole) were dissolved in a mixture of hot ethanol (1.3 L) and water (130 ml). To the solution n-pentyl bromide (6.31 ml, 51 mmole) was added and the mixture was refluxed for 20 hours. At this point a KOH solution (5 g of KOH dissolved in 26 ml of ethanol and 10 ml of water) was added and the mixture was refluxed for 2 hours. The solution was then cooled to room temperature and poured into 2.8 L of water. The resulting solution was neutralized by adding concd HCl and a solid precipitate was collected by vacuum filtration. The crude solid product was dissolved in hot glacial acetic acid (250 ml), and of any insoluble material removed by vacuum filtration. The filtered solution containing recrystallized product was then heated again to dissolve all the crystals. The solution was further heated until the volume of the solution was reduced to 100 ml. At this point, the solution was slowly cooled down to room temperature and the resulting precipitate was collected by vacuum filtration. The product was washed with water and dried under vacuum. MW: 284.36; Yield: 51%; $^1$H NMR (300 MHz, d$_6$-DMSO) δ 0.94(t, J=7.01 Hz, 3H), 1.3–1.8(m, 6H), 3.99(t, J=6.52 Hz, 2H); 7.02(d, J=78.73 Hz, 2H); 7.62(d, J=8.65 Hz, 2H); 7.71(d, J=8.35 Hz, 2H); 7.98(d, J=8.23 Hz, 2H); 12.93(s, 1H).} and DPTS (DPTS is 4-dimethylaminopyridinium p-toulenesulphonic acid) (603 mg, 2.2 mmol) in dry CH$_2$Cl$_2$ (62 ml) was added 1.07 ml of DIPC (DIPC is N,N'-diisopropylcarbodiimide) (6.8 mmol) at room temperature under a nitrogen atmosphere. The mixture was stirred for 36 hours at room temperature and the solid precipitate (urea) was removed by vacuum filtration, followed by evaporation of the solvent. The residue was purified by flash column chromatography using a mixture of 2% ethyl acetate in $CH_2Cl_2$ as eluent to give 2.16 g (80% yield) of the title compound as a solid, mp 84° C.

MS (FAB): 660 (MH+);

$^1$H NMR (300 MHz, CDCl$_3$, TMS) δ 0.93–0.97 (m, 3H), 1.38–1.75 (m, 14H), 1.59 (s, 9H), 2.63 (t, 2H), 2.78 (m, 1H), 2.94 (t, 2H), 4.04 (t, J=6.5 Hz, 2H), 7.02 (d, J=8.7 Hz, 2H), 7.15 (d, J=8.5 Hz, 2H), 7.24 (d, J=8.7 Hz, 2H), 7.31 (d, J=8.3 Hz, 2H), 7.62 (d, J=8.7 Hz, 2H), 7.71 (d, J=8.4 Hz, 2H), 7.98 (d, J=8.2 Hz, 2H), 8.25 (d, J=8.4 Hz, 2H);

$^{13}$C NMR (75 MHz, CDCl$_3$) δ 14.07 (CH$_3$), 22.49 (CH$_2$), 27.00 (CH$_2$), 28.20 (H$_3$), 28.56 (CH$_2$), 28.96 (CH$_2$), 31.07 (CH$_2$), 31.74 (CH$_2$), 33.55 (CH$_2$), 35.13 (CH$_2$), 38.30 (CH$_2$), 68.14 (CH$_2$), 81.06 (C), 114.97 (CH), 121.44 (C), 121.49 (CH), 126.57 (CH), 127.57 (C), 128.38 (CH), 128.90 (CH), 129.33 (CH), 129.90 (CH), 130.69 (CH), 131.08 (C), 131.97 (C), 139.87 (C), 141.61 (C), 145.91 (C), 149.01 (C), 159.56 (C), 165.31 (C), 165.46 (C);

Elemental Analysis: Calculated for C$_{43}$H$_{49}$O$_5$N (Mw=660.4) C,78.27; H,7.19; N,2.12 Found: C,78.26; H,7.52; N, 2.15.

Step 4
4-[(2R)-2-cyano-7-(4-((4-pentyloxy-4'-biphenyl)carbonyloxy) phenyl)heptylidene] benzoic acid To a solution of tert-butyl 4-[(2R)-2-cyano-7-(4-((4'-pentyloxy-4-biphenyl)carbonyloxy)phenyl)heptylidene] benzoate (4) (2.1 g, 3.2 mmol) in dry $CH_2Cl_2$ (10 ml) was added 3.3 ml of CF$_3$CO$_2$H (TFA) at room temperature under a nitrogen atmosphere. The solution was stirred for 4.5 hours and then solvent and the TFA was removed by rotary evaporation and high vacuum. The remaining solid was dissolved in a minimum amount of $CH_2Cl_2$, followed by the addition of pentane until permanent cloudiness was observed. The precipitate was collected by vacuum filtration, and dried in a vacuum desiccator to give 1.5 g (79% yield) of the title compound, mp 180° C.

MS (FAB) 605 (MH+);

$^1$H NMR (300 MHz, CDCl$_3$, TMS) δ 0.95 (t, J=6.9 Hz, 3H), 1.37–1.85 (m, 14H), 2.64 (t, J=7.5 Hz, 2H), 2.66 (m, 1H), 2.76 (t, J=5.2 Hz, 2H), 4.02 (t, J=6.6 Hz, 2H), 7.02 (d, J=8.6 Hz, 2H), 7.15 (d, J=8.4 Hz, 2H), 7.26 (d, H=8.1 Hz, 2H), 7.36 (d, J=8.1 Hz, 2H), 7.61 (d, J=8.1 Hz, 2H), 7.69 (d, J=8.2 Hz, 2H), 8.10 (d, J=8.0 Hz, 2H), 8.24 (d, J=8.2 Hz, 2H);

$^{13}$C NMR (75 MHz, CDCl$_3$) δ 14.07 (CH$_3$), 22.50 (CH$_2$), 26.96 (CH$_2$), 28.22 (CH$_2$), 28.50 (CH$_2$), 28.96 (CH$_2$), 31.03 (CH$_2$), 31.87 (CH$_2$), 33.43 (CH), 35.12 (CH$_2$), 38.39 (CH$_2$), 68.15 (CH$_2$), 114.98 (CH), 121.34 (C), 121.51 (CH), 125.72 (C), 126.57 (CH), 127.55 (C), 128.39 (CH), 129.23 (CH), 129.34 (CH), 130.71 (CH), 131.96 (C), 139.86 (C), 143.22 (C), 145.91 (C), 149.02 (C), 159.56 (C), 165.35 (C), 171.68 (C);

Elemental Analysis: Calculated for C$_{39}$H$_{41}$O$_5$N (Mw=603.8): C,77.58; H,6.85; N,2.31 Found: C,77.39; H,6.95; N,2.37

Step 5
4-[4-(2R)-2-cyano-7-(4-((4'-pentyloxy-4-biphenylcarbonyloxy)phenyl)heptylidene)phenylcarbonyloxy]benzaldehyde To a suspension of DPTS (85 mg, 0.31 mmol), 4-[(2R)-2-cyano-7-(4-((4'-pentyloxy-4-biphenyl)carbonyloxy)phenyl)heptylidene] benzoic acid (5) (300 mg, 0.5 mmol) and 4-hydroxybenzaldehyde (3.6 eq) in $CH_2Cl_2$ at room temperature was added 130 ml of DIPC (0.83 mmol) with vigorous stirring under a nitrogen atmosphere. After being stirred for 17 hours at room temperature, the solid precipitate (urea) was removed by vacuum filtration followed by evaporation of solvent. The solid residue was dissolved in a minimum amount of $CH_2Cl_2$, and then the product was purified by flash column chromatography using a mixture of 1% acetone in $CH_2Cl_2$ as eluent to give 0.316 mg (89% yield) of the title compound as a solid.

MS (FAB) 708(MH+);

$^1$H NMR (300 MHz, CDCl$_3$ TMS) δ 0.95 (t, J=7 Hz, 3H), 1.36–1.85 (m, 14H), 2.66 (t, J=7.4 Hz, 2H), 2.82 (m, 1H), 2.98 (d, J=6.3 Hz, 2H), 4.01 (t, J=6.4 Hz, 2H), 7.01 (d, J=8.7 Hz, 2H), 7.17 (d, J=8.4 Hz, 2H), 7.23 (d, J=8.5 Hz, 2H), 7.41 (m, 4H), 7.57 (d, J=8.7 Hz, 2H), 7.68 (d, J=8.4 Hz, 2H), 7.98 (d, J=8.5 Hz, 2H), 8.24 (m, 4H), 10.03 (s, 1H);

$^{13}$C NMR (75 MHz, CDCl$_3$) δ 14.08 (CH$_3$), 22.49 (CH$_2$), 28.98 (CH$_2$), 28.22 (CH$_2$), 28.48 (CH$_2$), 28.96 (CH$_2$), 31.01 (CH$_2$), 31.85 (CH$_2$), 33.49 (CH), 35.11 (CH$_2$), 38.39 (CH$_2$), 68.14 (CH$_2$), 114.98 (CH), 121.25 (C), 121.51 (CH), 122.54 (CH), 126.57 (CH), 127.54 (C), 127.96 (C), 128.37 (CH), 129.34 (CH), 129.46 (CH), 130.68 (CH), 130.78 (CH), 131.29(CH), 131.92 (C), 134.08 (C), 139.82 (C), 143.52 (C), 145.92(C), 149.04(C), 155.62(C), 159.58(C), 164.18 (CH), 165.31 (C), 190.93 (C), 190.95 (C);

Elemental Analysis: Calculated for C$_{46}$H$_{45}$O$_6$N (Mw=707.8); C,78.05; H,6.41; N,1.98 Found: C,77.33; H,6.41; N,1.89.

Figure 3:
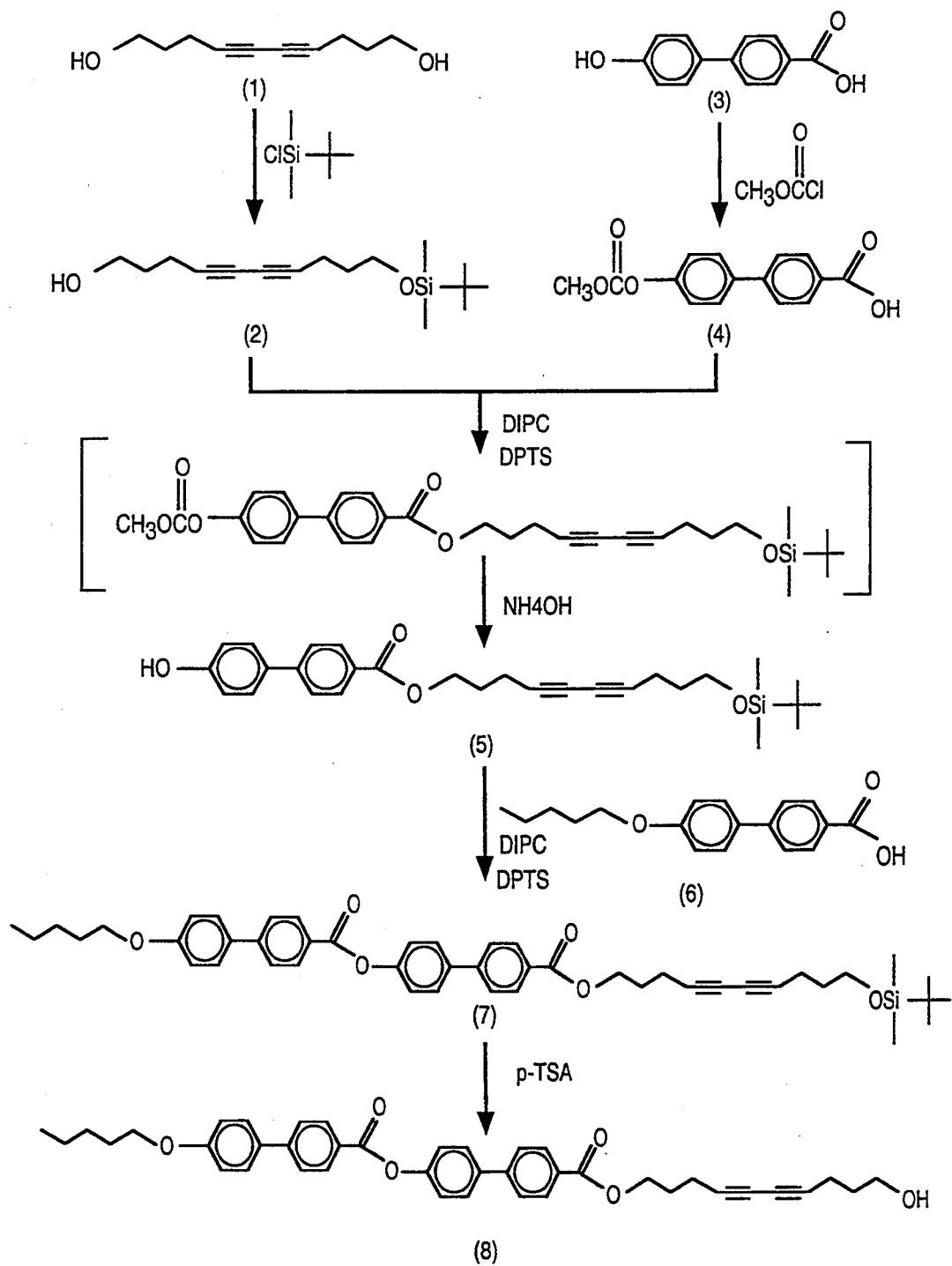
FIG. 3 shows the synthesis of (12-hydroxy-5,7-dodecadiynyl) 4'-[(4'-pentyloxy-4-biphenyl)carbonyloxy]-4-biphenylcarboxylate.

Synthesis 2 below shows the synthesis of (12-hydroxy-5,7-dodecadiynyl)-4'-[(4'-pentyloxy-4-biphenyl)carbonyloxy]-4-biphenylcarboxylate. FIG. 3 shows the synthesis in diagrammatic form.

Synthesis 2 (12-Hydroxy-5,7-dodecadiynyl) 4'-[(4'-pentyloxy-4-biphenyl)carbonyloxy]-4-biphenyl-carboxylate

Step 1
12-(Tert-Butyldimethylsilyloxy)-5,7-dodecadiyn-1-ol 5,7-Dodecadiyn-1,12-diol (1) (4 g, 20.6 mmol) and imidazole (2.8 g, 41 mmol) were dissolved in dimethylformamide (15 ml). To the solution, tert-butyldimethylsilylchloride (2.38 g, 18.8 mmol) was added at once. The solution was stirred for 20 hours at room temperature under a nitrogen atmosphere. At this point, the reaction mixture was transferred into a separatory funnel along with dichloromethane (100 ml) and washed with saturated sodium bicarbonate solution and water successively. The organic layer was died (MgSO$_4$) and concentrated followed by purification of the residue by flash column chromatography (silica gel, 7% acetone in dichloromethane) affording 3.17 g of a pale yellow oil (55% yield) of the title compound.

Molecular Weight: 308.53 (C$_{18}$H$_{32}$O$_2$Si)

$^1$H NMR (300 MHz, CDCl$_3$) δ 0.04 (s, 6H), 0.88 (s, 9H), 1.5–1.8 (m, 8H), 2.2–2.4 (m, 4H), 3.6–3.8 (m, 4H).

Step 2 4'-(methoxycarbonyloxy)-4-biphenylcarboxylic acid

4'-Hydroxy-4-biphenylcarboxylic acid (3) (4 g, 18.67 mmol) and sodium hydroxide (1.64 g, 41.1 mmol) were dissolved in water (50 ml) and ethanol (98 ml) at −10° C. To the solution, methyl chloroformate (1.73 ml, 22.4 mmol) was added and the solution was maintained at −5° C. The solution was stirred for 40 minutes and a mixture of water and hydrochloric acid (1:1) was added until the solution became acidic. The solid precipitate was collected by vacuum filtration, washed several times with distilled water and dried to yield 4.72 g (yield 95.5%) of the title compound.

Molecular Weight: 272.25 ($C_{15}H_{12}O_5$)
Melting Point: Decomposes before melting
$^1$H NMR (300 MHz), DMSO-$d_6$) δ 3.842 (s, 3H), 7.36 (d, J=8.68 Hz, 2H), 7.78 (d, J=8.70 Hz, 2H), 7.80 (d, J=8.44 Hz, 2H), 8.03 (d, J=8.65 Hz, 2H)
Elemental Analysis: Calculated for C,66.17; H,4.44 Found C,66.19; H,4.45

Step 3 [12-(Tert-butyldimethylsilyloxy)-5,7-dodecadiynyl]4'-hydroxy-4-biphenylcarboxylate 4'-(Methoxycarbonyloxy)-4-biphenylcarboxylic acid(4) (1.33 g, 4.89 mmol) and DPTS (0.477 g, 1.62 mmol) were suspended in dichloromethane (60 ml). To the solution, DIPC (1.52 ml, 9.72 mmol) was added followed by the addition of 12-(tert-butyldimethylsilyloxy)-5,7-dodecadiyn-1-ol (2) (1.5 g, 4.86 mmol), which was diluted in dichloromethane (3 ml). After stirring for 12 hours at room temperature under a nitrogen atmosphere, the contents were poured into a separatory funnel and washed with water, dried (MgSO$_4$) and concentrated. The crude intermediate was purified by flash column chromatography (silica gel, dichloromethane) and concentrated. The intermediate was then diluted with dichloromethane (20 ml) and a mixture of ammonium hydroxide (29%) aqueous solution, (15 ml) and ethanol (50 ml) was added. After stirring for 2.5 hours, the solution was washed with saturated sodium bicarbonate and neutralized with hydrochloric acid (1N). The product was then extracted with dichloromethane, dried (MgSO$_4$) and concentrated to afford 1.9 g of a white solid product (77.5% yield) of the title compound.

Molecular Weight: 504.75 ($C_{31}H_{40}O_4Si$)
MP: 64° C.
$^1$H NMR δ (s, 6H), 0.88 (s, 9H), 1.6–2.0 (m, 8H), 2.3–2.5 (m, 4H), 3.62 (t, J=5.80 Hz, 2H), 4.35 (t, J=6.37 Hz, 2H), 6.94 (d, J=8.67 Hz, 2H), 7.53 (d, J=7.63 Hz, 2H), 7.61 (d, J=8.73 Hz, 2H), 8.08 (d, 8.32 Hz, 2H).
Elemental Analysis: Calculated for C,73.77; H,7.99 Found C,73.88; H,7.97

Step 4 [12-(Tert-butyldimethylsilyloxy)-5,7-dodecadiynyl] 4'-[(4'-pentyloxy-4-biphenyl)carbonyloxy]-4-biphenylcarboxylate 4'-Pentyloxy-4-biphenylcarboxylic acid (6)(See Sythesis 1, Step 3 for the synthesis of this compound) (310 mg, 1.09 mmol), [12-(tert-butyldimethylsilyloxy)-5,7-dodecadiynyl]-4'-hydroxy- 4-biphenylcarboxylate(5) (500 mg, 0.99 mmol) and DPTS (128 mg, 0.435 mmol) were suspended in chloroform (10 ml) at room temperature under a nitrogen atmosphere. To the solution DIPC (0.256 ml, 1.63 mmol was added at once via a syringe. After stirrng the reaction mixture for twenty hours, the solid precipitate was removed by vacuum filtration. The solution was then dried (MgSO$_4$) and concentrated. The residue was purified by flash column chromatography (silica gel, 33% petroleum ether in dichloromethane) to give 3.05 g of a white solid product (80% yield) of the title compound.

Molecular Weight: 771.09 ($C_{49}H_{58}O_6Si$)
$^1$H NMR (300 MHz, CDCl$_3$) δ 0.042 (s, 6H), 0.89 (s, 9H), 0.95 (t, J=7.01 Hz, 3H), 1.3–2.0 (m, 14H), 2.2–2.3 (m, 2H), 2.37 (t, J=6.9H, 2H), 3.62 (t, J=5.59 Hz, 2H), 4.03 (t, J=6.57, 2H), 4.37 (t, J=6.21 Hz, 2H), 7.01 (d, J=8.85 Hz, 2H), 7.35 (d, J=8.46 Hz, 2H), 7.61 (d, J=8.62 Hz, 2H), 7.6–7.7 (m, 6H) 8.12 (d, J=8.20 Hz, 2H), 8.26 (d, J=8.33 Hz, 2H).
Elemental Analysis: Calculated C,76.33; H,7.58; Si,3.64 Found C,76.38; H,7.58; Si,3.61

Step 5 (12-Hydroxy-5,7-dodecadiynyl) 4'-[(4'-pentyloxy-4-biphenyl)carbonyloxy]-4-biphenylcarboxylate To a solution of (7) (0.4 g, 0.519 mmol), tetrahydrofuran (6 ml) and water (0.28 ml), p-TSA (p-TSA is paratoluene sulfonic acid monohydrate) (28 mg, 0.147 mmol) was added at once at room temperature. After stirring for twenty hours, the contents were transferred into a separatory funnel along with dichloromethane (20 ml). The organic layer was washed with water, dried (MgSO$_4$) and concentrated. The crude product was purified by flash column chromatography (silica gel, 5% acetone in dichloromethane). 280 mg of the title compound were obtained (82%).

Molecular Weight: 656.83 ($C_{43}H_{44}O_6$)
Elemental Analyisis: Calculated: C,78.63; H,6.75 Found C,78.62; H,6.74
$^1$H NMR (300 MHz, DMSO $d_6$) δ 0.87 (t, J=6.82 Hz, 3H), 1.3–2.0 (m, 14H), 2.0–2.1 (m, 2H), 2.29 (t, J=6.74 Hz, 2H), 3.80 (t, J=6.87 Hz, 2H), 3.94 (t, J=6.49 Hz, 2H), 4.27 (t, J=6.39 Hz, 2H), 6.93 (d, J=8.51 Hz, 2H), 7.28 (t, J=8.49 Hz, 2H), 7.56 (d, J=8.37 Hz, 2H), 7.6–7.7 (m, 6H), 8.01 (d, J=8.23 Hz, 2H), 8.14 (d, J=8.30 Hz, 2H)

Figure 4:
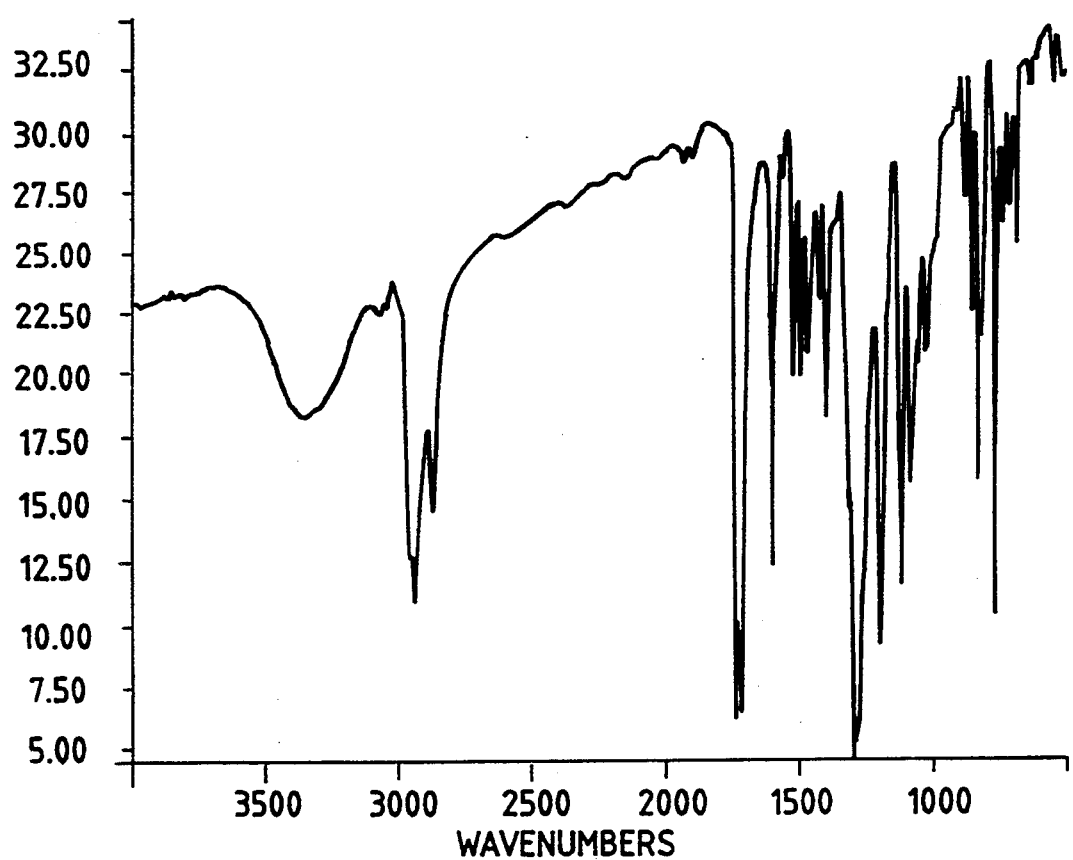
FIG. 4 is an IR spectrum of the polymeric form of the compound (12-hydroxy-5,7-dodecadiynyl) 4'-[(4'-pentyloxy-4-biphenyl)carbonyloxy]-4-biphenylcarboxylate.

FIG. 4 shows an IR spectra of the compound (12-hydroxy-5,7-dodecadiynyl) 4'-[(4'-pentyloxy-4-biphenyl)carbonyloxy]-4-biphenylcarboxylate.

Typically, polymerization of the title compound occurs spontaneously in bulk as the title compound is isolated from solution. However, the title compound may be polymerized extensively and rapidly by irradiation with ultraviolet light.

The foregoing specification, including the specific embodiments and examples is intended to be illustrative of the present invention not limiting. Numerous other variations and modifications can be effected without departing from the true spirit and scope of the present invention.

What is claimed is:

1. The compound 4-[4-(2R)-2-cyano-7-(4'-pentyloxy-4-biphenylcarbonyloxy)phenylheptylidene)phenylcarbonyloxy]benzaldehyde.

2. The compound (12-hydroxy-5,7-dodecadiynyl) 4'-[(4'-pentyloxy-4-biphenyl)carbonyloxy]-4-biphenylcarboxylate.

* * * * *